United States Patent [19]

Lindahl et al.

[11] 4,303,651
[45] Dec. 1, 1981

[54] HEPARIN FRAGMENTS HAVING SELECTIVE ANTICOAGULATION ACTIVITY

[75] Inventors: Ulf P. F. Lindahl, Uppsala; Gudrun E. Bäckström, Alunda; John Y. L. Thunberg, Uppsala; Lars-Åke Fransson, Lund; Lars-Olov Andersson, Knivsta; Erik Y. Holmer, Bromma; Inga H. Sandberg, Sollentuna; Ewa G. Söderström, Saltsjöbaden, all of Sweden

[73] Assignee: Kabi AB, Stockholm, Sweden

[21] Appl. No.: 109,936

[22] Filed: Jan. 4, 1980

[30] Foreign Application Priority Data

Jan. 8, 1979 [SE] Sweden ............................. 7900164

[51] Int. Cl.$^3$ ..................... A61K 31/725; C08B 37/10
[52] U.S. Cl. ...................................... 424/183; 536/21
[58] Field of Search ........................... 424/183; 536/21

[56] References Cited

U.S. PATENT DOCUMENTS

| | | | |
|---|---|---|---|
| 3,066,076 | 11/1962 | Monnier | 536/21 |
| 3,135,660 | 6/1964 | Bush et al. | 536/21 |
| 3,810,781 | 5/1974 | Eriksson et al. | 424/183 |
| 3,835,112 | 9/1974 | Mardiguian et al. | 536/21 |
| 3,891,622 | 6/1975 | Mardiguian et al. | 424/183 |

*Primary Examiner*—Johnnie R. Brown
*Attorney, Agent, or Firm*—Pollock, Vande Sande & Priddy

[57] ABSTRACT

Heparin fragments having selective anticoagulation activity having 14–18 sugar units, the disaccharide unit L-iduronosyl-2-O-sulphate-N-sulpho-U-glucosamine-6-O-sulphate being the main component, and where unsulphated L-iduronic acid is in a position situated 3–5 sugar units from the unreducing terminal. Pharmaceutical compositions containing such heparin fragments. Processes for the preparation of the heparin fragments.

6 Claims, No Drawings

HEPARIN FRAGMENTS HAVING SELECTIVE ANTICOAGULATION ACTIVITY

The present invention relates to heparin fragments which have been shown to possess selective anticoagulation activity, a process for the preparation thereof, and therapeutical compositions containing such fragments.

Heparin is a sulphate-containing polysaccharide which on a large scale is isolated from intestinal mucus from swine of lung from cattle. It has for several decades been used clinically as an agent for the treatment and prevention of thrombosis. In spite of the fact that the use of heparin in thrombosis prophylaxis and therapy is still increasing, this form of treatment is far from unproblematic. An important problem is that the dosage must be balanced in such a manner that a good thrombosis protection is obtained simultaneously as bleeding complications are avoided. A difficulty in this contect is the great individual variation between different patients; this is in turn probably dependent on the fact that the heparin is bound to a varying degree to other components in the blood plasma and thereby neutralised. Another problem is that the preventive heparin treatment suffers from limitd success. A third problem with the present type of heparin is its weak effect on arterial thrombosis. At said type of thrombosis the thrombocyte aggregation is a more dominating feature than at the venous thrombosis where heparin gives a good effect. Standard heparin stimulates to a certain extent thrombocyte aggregation and accordingly gives a negative effect in said respect.

The mechanism of the anticoagulation activity of the heparin is now essentially known. The blood coagulation is based on a cascade like process where a number of proteolytic enzymes are activating each other in a definite sequence; in the last stage fibrinogen is converted under the action of the proteolytic enzyme thrombin to insoluble fibrin, the foundamental structure in a blood coagel. Heparin forms a complex with a plasma protein, and this complex inhibits most of the enzymes in the coagulation cascade.

It has been recently shown that heparin fractions of different molecular weights influence the coagulation process in different ways [L.-O. Andersson et al., Tromb. Res. 9, 575 (1976)]. This initiated a study of the possibilities to develop heparin fractions having a more selective action. Treatment of standard heparin with nitrous acid in dimethoxyethane (glyme) at a low temperature and for a certain definite period of time has resulted in a special fragment of heparin possessing a considerably higher selective action than standard heparin. This heparin derivative has a very small effect on the inhibition of thrombin, while the inhibition of activated coagulation factor X is highly accelerated. Coagulation factor X takes a central position in the middle of the coagulation cascade and the inhibition thereof is by many considered especially important to obtain an effective thromsis-preventing effect [S. Wessler, Thromb. Diath. Haemorrh. 33, 81 (1974)].

It has further quite unexpectedly been shown that said type of fragments are not neutralised by the blood components to the same extent as standard heparin. This results in, inter alia, a more efficient utilisation of the anticoagulation activity of this type of fragments compared to the present clinically used heparin preparations. Further, also the dosage is easier to perform, as the individual variation of heparin-neutralising effect is less important to take into consideration. A further surprising property of the fragment is that its thrombocyte aggregation-inducing activity is much lower than that which is usually shown by heparin. Therefore, it is probable that this type of fragment is a better anticoagulation agent than standard heparin for preventive treatment and treatment of arterial thromboses. It may also be assumed that the reduced influence on the thrombocytes may lead to a lowered risk of bleeding complications.

It should also be noted that the capacity of the heparin to release the enzyme lipoprotein lipase is strongly dependent on the molecular weight. Therefore, it may be assumed that the low molecular weight heparin fragment has a further valuable property in that it to a lesser extent than standard heparin increases the contents of free fatty acids in the blood.

This speical type of heparin fragments may be prepared in several different ways. One of the methods (a) comprises treatment of standard heparin with nitrous acid in dimethoxyethane as mentioned above. Said method gives this type of fragments together with a series of inactive fragements. The active fragments may then be freed from inactive elements, such as by affinity chromatography on matrix-bound antithrombin III [Höök et al., FEBS Lett. 66, 90 (1976); Hopwood et al., FEBS Lett. 63, 51 (1976); L.-O. Andersson et al., Thromb. Res. 9, 575 (1976)]. other ways of preparing fragments are: (b) via periodate oxidation at low pH and low temperature; (c) via partial depolymerisation with heparinase; (d) via partial depolymerisation of heparin by esterification of carboxyl groups and subsequent alkaline $\beta$-elimination; (e) via partial depolymerisation of heparin by partial N-desulphatation and subsequent deamination with nitrous acid at a pH value of 3.9. Methods (a) and (b) are described in the examples.

The active fragments are characterised in that they contain from 14 to 18 sugar units. Structural analysis shows the same main structural components as in standard heparin, i.e. L-iduronosyl-2-O-sulphate-(1$\alpha$-4)-N-sulpho-D-glucosamine-6-O-sulphate as the dominating saccharide unit. However, the amount of unsulphated iduronic acid is considerably higher than in the starting material. Periodate oxidation has shown that the component takes a definite position in the molecule situated from 3 to 5 sugar units counted from the unreducing terminal. The active fragments have the structure (U-G)$_n$-I-G-(U-G)$_m$ where n is 1 or 2 and m is 5 or 6, I is unsulphated L-iduronic acid, U is L-iduronic acid-2-O-sulphate and G is N-sulpho-D-glucosamine-6-O-sulphate. A few U units may lack O-sulphate or be replaced by D-glucuronic acid and, similarly, a few G units may lack O-sulphate or be replaced by N-acetyl-D-glucosamine units. Reducing or unreducing terminal units may vary with the type of method of preparation used; thus e.g., deaminitive splitting of heparin leads to the formation of 2,5-anhydro-D-mannose in reducing terminal position. The active fragments may be characterised by means of physico-chemical methods, such as determination of mobility in an electric field and UV, IR and NMR spectra. However, the numerical values obtained do not give complete information, as also coagulation-inactive fragments substantially show similar characteristics. This depends on the fact that the biologic activity is derived from a specific sequence of the sugar residues where the position of the unsulphated uronic acid is especially important. Thus, only a gross composition and size does not warrant that the component is active.

The invention is further illustrated by the following examples.

EXAMPLE 1

Preparation of heparin fragments by depolymerisation of standard heparin with nitrous acid Heparin (0.5 g) isolated from swine intestines and dissolved in 150 ml of water is chilled to +40° C. and brought to pass through a 3×7 cm column of Dowex ®50 W-28 (H+ form), 200–400 mesh. The column is then washed with 100 ml of water and the washing liquid is combined with the sample. To the sample there are added 250 ml of dimethoxyethane (glyme) chilled to −20° C. and 10 ml of isoamyl nitrite and the mixture having a temperature of about −10° C. is allowed to stand for two minutes. The reaction is then discontinued by the addition of 10 ml of 10% Na+-acetate. After addition of 5.2 liters of ethanol precipitated carbohydrate (heparin derivatives) is recovered by centrifugation. The product is dissolved in 500 ml of 0.05M NaCl - 0.05M Tris-HCl, pH 7.4. This solution is fractionated, divided into 100 ml portions, by affinity chromatography on a column containing 75 ml of anti-thrombin-agarose-Sepharose ® (Pharacia Fine Chemicals, Uppsala, Sweden) (about 5 mg of protein per ml gel). The column is eluated by a salt gradient (500 ml of 0.05M NaCl-0.05M Tris-HCl in the mixing vessel; 500 ml of 3M NaCl-0.05M Tris-HCl in the reservoir), the major part of the applied material either passing unretardedly through the column or being eluated at a low ion strength (less than 0.4M NaCl); this material has no biologic activity. The active components (purified heparin derivatives) are eluated in a wide top between 0.05M NaCl and 3M NaCl corresponding to about 4% of the starting material. These fractions are pooled and desalted by gel chromatography.

Heparin derivatives prepared and purified in said manner have a molecular size corresponding to that of a tetradeca-octadecasaccharide (molecular weight 3600–4800). Structural analysis show the same structural components as in the starting material, L-iduronosyl-2-O-sulphate-(1α-4)-N-sulpho-D-glucosamine-6-O-sulphate being the dominating disaccharide unit. However, the amount of unsulphated iduronic acid has increased from about 6% in the starting material to about 16%. As to other aspects the structure agrees with the above description.

Example 2

Partial depolymerisation of heparin or heparin by-product by periodate oxidation at a pH value of 3° and 4° C. and subsequent alkali-treatment and reduction Under these conditions the polysaccharide chain is split at D-glucuronic acid units resulting in only moderate loss of anticoagulation activity (Fransson and Lewis, FEBS Letters, 1979, in press). Standard Heparin (0.5 g) is dissolved in 250 ml of a solution (4° C.) containing 0.02M NaIO$_4$, 0.2M NaClO$_4$ and 0.05M Na+- citrate buffer, pH 3.0. After three hours incubation in dark at +4° C. the oxidation is discontinued by the addition of a molar excess of D-mannitol and, then, the solution is dialysed and freeze-dried. Splitting of the polysaccharide chains at oxidised D-glucuronic acid units is effected by treament of the product with alkali (5 mg/ml of aqueous solution adjusted to pH 12 with 1M NaOH) at room temperature. After ten minutes the solution is neutralised with 1M acetic acid and, then, the material is desalted by gel chromatography on dextran material (Sephadex ® G-25, Pharmacia Fine Chemicals, Uppsala, Sweden). The product obtained can be reduced with sodium borohydride.

Heparin treated in said manner is considerably depolymerised compare to the starting material; gel chromatography shows that the resulting fragments have a size corresponding to 10–25 sugar units and, therefore, they ae somewhat larger than the fragments isolated after treatment with nitrous acid according to Example 1. Totally about 20% of the uronic acids in the polysaccharide are destroyed under the periodate oxidation (pH 3, 4° C., 3–6 hours). Purification by affinity chromatography of the oxidation products on antithrombinagarose-Sepharose ® gave a yield of about 30% of high-affinity material after three hours and a yield of 15% after six hours oxidation. The products thus obtained had an antifactor $X_a$-potentiating effect determined according to Example B in plasma of more than 1000 units/mg compared to 3rd International Heparin Standard.

Studies on anticoagulation activity

The heparin fragment prepared according to Example 1 was studied in view of its capacity to: (A) accelerate the inhibition of the coagulation enzyme thrombin; (B) accelerate the inhibition of activated coagulation factor X; (C) prolong the coagulation time in the blood plasma coagulation test APTT (Activated Partial Thromboplastine Time); (D) be neutralised by blood plasma components; and (E) influence the aggregation of thrombocytes.

EXAMPLE A

Inhibition of thrombin

The capacity of the heparin fragment to potentiate the inhibition of thrombin with antithrombin III was analysed according to a modification of a method by Teien et al. (Thrombosis Research 11, p. 107–117, 1977). The heparin fragment was found to have a specific activity of less than 20 E/mg compared to 120–170 E/mg for standard heparin.

EXAMPLE B

Inhibition of activated factor X

The capacity of the heparin fragment to potentiate the inhibition of activated factor X in plasma and in pure antithrombin III was studied according to a modified version of a method by Teien et al. (Thrombosis Research 8, 413, 1976). The heparin fraction was shown to have a specific activity of 500 E/mg in a pure antithrombin III system and 2100 E/mg in a plasma system compared to 120–170 E/mg for standard heparin.

EXAMPLE C

Prolongation of the coagulation time

The capacity to prolong the coagulation time of blood plasma was studied according to the APTT (Activated Partial Thromboplastine Time) method [Andersson et al., Thromb. Res. 9, 575 (1976)]. The heparin fragment showed a specific activity of less than 20 E/mg compared to 3rd International Heparin Standard. Standard heparin shows a specific activity in the range 120–170 E/mg.

EXAMPLE D

Neutralisation of heparin fragments in blood plasma

The heparin-neutralising effect of plasma components was studied by measuring the effect of heparin and the heparin fragment in plasma and in a pure antithrombin system. This was performed by measuring the amount of activated factor X inhibited in the two systems in the presence of a certain amount of heparin or heparin fragment. The activity of the heparin fragment showed a 15% neutralisation by plasma components, while the corresponding value of standard heparin was shown to be 75%.

EXAMPLE E

Thrombocyte influence

The capacity of the heparin fragment to aggregate thrombocytes at critical ADP (Adenosine DiPhosphate) concentrations was substantially studied according to Beck, E. A. (Thromb Haem Stuttg. 1977, 38, 578). It was shown that the thrombocyte-aggregating capacity of the heparin fragment was ten times lower than that of standard heparin, calculated on the weight.

The heparin fragment according to the invention is incorporated into pharmaceutical preparations for clinical use, preferably in aqueous solution for injection or in ointment preparations for administration via the skin and mucous membranes.

We claim:

1. Heparin fragments having 14–18 sugar units, wherein the main component is the disaccharide unit L-iduronosyl-2-O-sulphate-N-sulpho-D-glucosamine-6-O-sulphate, and where unsulphated L-iduronic acid is in a position situated 3–5 sugar units from the unreducing terminal and is followed by a unit selected from the group consisting of N-sulpho-D-glucosamine sulphate and N-acetyl-glucosamine in sulphated and unsulphated form.

2. Heparin fragments having the structure $(U-G)_n$-I-G-$(U-G)_m$ where n is 1 or 2 and m is 5 or 6, I is unsulphated L-iduronic acid, U is L-iduronic acid-2-O-sulphate, and G is N-sulpho-D-glucosamine-6-O-sulphate.

3. Pharmaceutical compositions for preventative treatment or treatment of arterial thrombosis containing heparin fragments having selective anticoagulation activity and containing 14–18 sugar units, wherein the main component is the disaccharide unit L-iduronosyl-2-O-sulphate-N-sulpho-D-glucosamine-6-O-sulphate, and where unsulphated L-iduronic acid is in a position situated 3–5 sugar units from the unreducing terminal and is followed by a unit selected from the group consisting of N-sulpho-D-glucosamine sulphate and N-acetyl-glucosamine in sulphated and unsulphated form in an amount sufficient for anticoagulation activity; and a pharmaceutical carrier.

4. Pharmaceutical composition for preventative treatment or treatment of arterial thrombosis containing heparin fragments of the structure $(U-G)_n$-I-G-$(U-G)_m$ where n is 1 or 2 and m is 5 or 6, I is unsulphated L-iduronic acid, U is L-iduronic acid-2-O-sulphate and G is N-sulpho-D-glucosamine-6-O-sulphate in an amount sufficient for anticoagulation activity; and a pharmaceutical carrier.

5. The composition of claim 3 or 4 wherein said carrier is water.

6. The composition of claim 3 or 4 which is in the form of an ointment.

* * * * *

UNITED STATES PATENT AND TRADEMARK OFFICE

CERTIFICATE EXTENDING PATENT TERM
UNDER 35 U.S.C. § 156

PATENT NO.      : 4,303,651

ISSUED          : December 1, 1981

INVENTOR(S)     : Ulf P. F. Lindahl et al.

PATENT OWNER :   Pharmacia Aktiebolag

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of

FIVE YEARS from the original expiration date of the patent, January 4, 2000, with all rights pertaining thereto as provided by 35 U.S.C. § 156(b).

I have caused the seal of the Patent and Trademark Office to be affixed this 31st day of May 1996.

Bruce A. Lehman
Assistant Secretary of Commerce and
Commissioner of Patents and Trademarks